United States Patent
Schulz et al.

(10) Patent No.: US 10,363,331 B2
(45) Date of Patent: Jul. 30, 2019

(54) STERILIZATION INDICATOR FOR A STERILE CONTAINER

(71) Applicant: Aesculap AG, Tuttlingen (DE)

(72) Inventors: Peter Schulz, Löffingen (DE); Stefan Schuster, Villingen-Schwenningen (DE); Stefan Thomas, Tuttlingen (DE)

(73) Assignee: Aesculap AG (DE)

( * ) Notice: Subject to any disclaimer, the term of this patent is extended or adjusted under 35 U.S.C. 154(b) by 322 days.

(21) Appl. No.: 15/031,843

(22) PCT Filed: Oct. 22, 2014

(86) PCT No.: PCT/EP2014/072616
§ 371 (c)(1),
(2) Date: Apr. 25, 2016

(87) PCT Pub. No.: WO2015/062924
PCT Pub. Date: May 7, 2015

(65) Prior Publication Data
US 2016/0263264 A1    Sep. 15, 2016

(30) Foreign Application Priority Data
Oct. 30, 2013    (DE) .................. 10 2013 111 979

(51) Int. Cl.
*A61L 2/28* (2006.01)
*A61B 50/30* (2016.01)
(Continued)

(52) U.S. Cl.
CPC .............. *A61L 2/28* (2013.01); *A61B 50/30* (2016.02); *A61B 2017/00867* (2013.01);
(Continued)

(58) Field of Classification Search
CPC ... A61L 2/28; A61L 2/26; A61B 50/30; A61B 50/31; A61B 50/36; A61B 2050/311; A61B 90/40
(Continued)

(56) References Cited

U.S. PATENT DOCUMENTS 4,539,929 A * 9/1985 Sestak ................. A61L 2/26
116/216
5,147,351 A * 9/1992 Wagner ................ A61L 2/26
292/284
(Continued)

FOREIGN PATENT DOCUMENTS

CN    2817846 Y    9/2006
CN    202409584 U  9/2012
(Continued)

OTHER PUBLICATIONS

German Search Report dated Mar. 31, 2014 for German Application No. 10 2013 111 979.4 with translation.
(Continued)

*Primary Examiner* — Steven A. Reynolds
*Assistant Examiner* — Javier A Pagan
(74) *Attorney, Agent, or Firm* — RatnerPrestia (57) ABSTRACT

A sterilization indicator for a sterile container includes a shape-memory element in the form of a compression spring, which, when a predetermined temperature is reached or exceeded, subjects an indicating unit to a defined axial compressive force. The indicating unit is biased by a restoring spring in the counter-direction of the shape-memory element by way of a restoring force which is smaller than the defined axial compressive force. A latching mechanism can be actuated by a closing or locking mechanism of the sterile container. Following or during the closing or locking of the sterile container, the latching mechanism retains the indi-
(Continued)

cating unit in a sterile position, once the unit has been moved into the sterile position by the shape-memory element. Upon opening or unlocking of the sterile container below the sterilization temperature, it frees the indicating unit, whereupon the restoring spring moves the indicating unit back into an unsterile position.

14 Claims, 7 Drawing Sheets

(51) Int. Cl.
    *A61B 17/00*     (2006.01)
    *A61B 50/00*     (2016.01)
    *A61B 90/00*     (2016.01)

(52) U.S. Cl.
    CPC . *A61B 2050/0067* (2016.02); *A61B 2090/081* (2016.02); *A61L 2202/182* (2013.01); *A61L 2202/24* (2013.01)

(58) Field of Classification Search
    USPC .......................................................... 206/363
    See application file for complete search history.

(56) References Cited

U.S. PATENT DOCUMENTS

| | | | |
|---|---|---|---|
| 2003/0211618 A1* | 11/2003 | Patel | A61L 2/07 436/38 |
| 2005/0183656 A1* | 8/2005 | Isaacson | A61B 18/12 116/216 |
| 2005/0265889 A1* | 12/2005 | Wu | A61L 2/20 422/3 |
| 2014/0224687 A1* | 8/2014 | Schuster | A61L 2/26 206/363 |

FOREIGN PATENT DOCUMENTS

| | | |
|---|---|---|
| DE | 3316141 | 11/1984 |
| DE | 3632674 | 4/1988 |
| DE | 202009010210 | 11/2009 |
| DE | 102009034992 | 2/2011 |
| DE | 102011054827 | 5/2013 |
| EP | 0412571 | 2/1991 |
| EP | 0849429 | 6/1998 |
| EP | 2305318 | 4/2011 |
| WO | 2013060667 | 5/2013 |

OTHER PUBLICATIONS

International Search Report dated Jan. 29, 2015 issued in related International Application PCT/EP2014/072616.
Written Opinion dated Jan. 29, 2015 issued in related International Application No. PCT/EP2014/072616.
Chinese Office Action for Chinese Application No. 201480060072.3, dated Jul. 5, 2018, with translation, 19 pages.
Notice of Allowance for U.S. Appl. No. 14/254,204, dated Oct. 12, 2016, 5 pages.
Non-Final Office Action dated Jun. 7, 2016 for U.S. Appl. No. 14/254,204, 13 pages.

* cited by examiner

STERILIZATION INDICATOR FOR A STERILE CONTAINER

RELATED APPLICATIONS

This application is the United States national phase of International Application No. PCT/EP2014/072616, filed Oct. 22, 2014, which is related to and claims the benefit of priority of German Application No. 10 2013 111 979.4, filed Oct. 30, 2013. The contents of International Application No. PCT/EP2014/072616 and German Application No. 10 2013 111 979.4 are incorporated by reference in their entireties for all purposes.

FIELD

The invention relates generally to sterile containers, and more particularly to a sterilization indicator for a sterile container.

BACKGROUND

It is known to use sterile containers usually adapted to be equipped/filled with surgical instruments intended for sterilization in medicine and especially in surgery. During the sterilizing operation the instruments are retained in the sterile container and are strongly heated at a particular temperature until microorganisms and the spores thereof possibly occurring on the surgical instruments have been killed. For ensuring and indicating to a user, such as the staff members who intend to utilize the sterile instruments in the operating theater, that the instruments have in fact completed a sterilizing operation and the use thereof constitutes no problem for a patient with respect to any risk of infection in prior art various embodiments of sterilization indicators for sterile containers have already been suggested.

From DE 33 16 141 A1, for example, an exclusively manually operable sterilization indicator is known in the form of a closure seal for a sterile container. The closure seal which is allowed to be accessed only by a defined group of persons indicates in its integer state attached to the sterile container that sterilized objects, especially surgical instruments, are provided within the sterilization container. However, it is a drawback of this type of sterilization indicator that the closure seal has to be manually applied after the sterilizing operation, has to be checked for integrity and has to be removed again or at least destroyed before the sterile container is opened. The sterilizing operation itself has to be accurately monitored for reliable assessment of the sterility by virtue of the manual application of the closure seal. In other words, the closure seal informs about the fact that the content of the sterile container underwent a sterilizing process. It cannot be inferred from the closure seal itself, however, whether the sterilizing process has been carried out in a correct and thus successful manner.

A different type of sterilization indicator is known from EP 0 412 571 B1, for example. There an (intelligent) sterilization indicator for a sterile container is described which comprises an indicating element for indicating completed sterilization of the content of the sterile container. For this purpose, the indicating element includes a spring made of memory alloy which exhibits spring tension when reaching or exceeding a predetermined temperature, preferably the sterilization temperature (>90° C.). A locking member is automatically transferred (without manual activity) by the suddenly applied spring tension to a closing position in which it is evident that sterilization has taken place (quantity reference function) and has also been carried out correctly (quality reference function).

It is a drawback, however, that a comparatively cost-intensive memory-alloyed coil spring (shape-memory element) is used for the sterilization indicator so that the spring has to be used several times. It has turned out, however, that the known spring cannot be brought into the tension-loaded memory position as often as required, but is subjected to considerable limitations regarding its service life and thus also regarding the possible sterilizing operations of the sterile container. The known sterilization indicator also turns out to constitute a problem to the effect that it is based on the principle of a comparatively inaccurate/inertly reacting rotary spring system that performs a circular actuating movement. This may result in wrong indications. Finally the sterilization indicator of EP 0 412 571 B1 has to be manually reset to its opening position when the sterile container is opened. Unless this is done, a subsequent sterilizing process cannot be documented as to quality any more.

SUMMARY

The invention, on the other hand, is based on the object to improve the reliability of a sterilization indicator for a sterile container using means of preferably simple design. It is one objective for the sterilization indicator to exhibit high operating safety and a most simple constructional design. It is another objective to ensure a comparatively large number of sterilizing and, resp., conditioning cycles.

This object is achieved by a sterilization indicator for a medical sterile container comprising features described herein.

The present invention is based on the principle/concept of the invention to design a shape-memory element in the form of an axially acting compression spring made of memory material which, when a predetermined temperature is reached/exceeded, subjects an indicating device/indicating unit to an axial compressive force, said indicating unit in turn being biased/adapted to be biased by means of a restoring spring (acting in a temperature-independent manner) in the direction counter to the shape-memory element. The two springs are adjusted to each other so that the (maximum) axial compressive force of the shape-memory element being reached at the predetermined temperature is higher than the spring force of the restoring spring. Finally a latching mechanism is provided which is (automatically) co-actuated by opening/closing and/or by the closing/locking mechanism of a sterile container and is designed such that after closing and/or locking the sterile container it retains the indicating unit in a sterile position, once said unit has been moved into the sterile position by the shape-memory element, and upon opening and/or unlocking of the sterile container it releases the indicating unit so that the restoring spring may move the indicating unit back into an unsterile position.

In terms of design, the afore-described concept of the invention can be basically realized by equipping the sterile container with a sterilization indicator in which the shape-memory element is positioned in the form of a helical compression spring along a push element (push rod) and is brought in compressing engagement with the same to which a (conventional) restoring spring (restoring helical compression spring) further applies a restoring force counteracting the shape-memory element (constantly, i.e. independently of temperature), the restoring force being smaller than a (maximum) compressive force of the shape-memory element upon reaching/exceeding a predetermined sterilization temperature inside the container. The push element in turn is coupled to or constitutes the indicating unit perceptible from outside which accordingly adopts a sterile position or unsterile position perceptible (in a visual, tactile etc. manner) from outside of the container in response to the container inside temperature and thus the (maximum) compressive force currently/temporarily exerted by the shape-memory element. It is noted that the restoring spring need not absolutely act directly on the push rod but may be operatively connected to the indicating unit, and hence by means of the indicating unit it exerts a restoring force on the same and thus also on the push element.

Finally the sterile container includes a cover/access door and/or a preferably manually operable closing/locking mechanism for opening/unlocking and closing/locking the container as well as a latching mechanism preferably in the form of a latch spring designed and/or placed so that it may be or is operatively engaged in the cover/access door and/or the closing/locking mechanism such that the latching mechanism/latch spring is (spring) biased (i.e. armed) initially only into a latching function (and not a latching position) upon closing and/or locking the sterile container (by a closing and/or locking actuation of the cover/access door and/or the closing/locking mechanism). The latching mechanism and, resp., the latch spring in turn is operatively connected to the indicating unit preferably via the push element or is integrated in the sterilization indicator so that when the sterile position is adopted (by the effect of the shape-memory element) the latching mechanism which is initially only biased (armed) into its latching function automatically (by biasing) adopts (snaps/triggers to) a latching position in which the sterilization indicator/indicating unit is locked in the sterile position (independently of the shape-memory element in this case) (even when the compressive force of the shape-memory element then decreases due to cooling of the container interior). When the closing/locking mechanism is opened/unlocked and/or the cover/access door is opened, the latching mechanism or, resp., the latch spring is released and is disengaged from the latched position (by the internal bias thereof or an external biasing spring) and in this way releases the sterilization indicator/indicating unit which is then moved into the unsterile position thereof by the restoring spring.

According to the foregoing remarks, the principle of a reusable sterilization indicator on sterile containers has been structurally realized only in combination with helical thermal bimetals so far. The switch-over of the indicator from an unsterile position to a sterile position is realized by a rotation of the indicator. Therefrom inaccuracies are resulting also due to unfavorable leverages especially in the responsive behavior of the sterilization indicator which in the worst case may involve that the indicator switches to the sterile position even though the required sterilization temperature has not yet been fully reached.

In accordance with the invention, however, according to an aspect of the invention a compressive spring having a memory effect (memory metal compression spring, preferably made of NiTi metal) is provided for realizing an axial movement along a plurality of helical windings. In this way low inertia can be obtained with changes in temperature, thus causing the risk of wrong status indication (sterile/unsterile) to be reduced. The (helical) compression spring usually is very reliable and has a long service life due to a comparatively low material load (per winding). The entire structure of the sterilization indicator according to the invention is inexpensive because only few components have to be used.

An advantageous development of the invention provides the arrangement of a push element in the form of an axially movable push rod or push plate in which at least the shape-memory element and preferably the restoring spring is in axial compressive engagement and which actuates an indicating unit perceptible from outside of the container into the sterile and/or unsterile position or which bears/supports or forms the indicating unit. Hence the absolutely required components are reduced to at least 3 parts, i.e. the push element for force transmission as well as for actuating or forming the indication (unit) and the two springs acting in opposite directions which may act on the push rod. This design is especially simple, is insusceptible to vibrations (as the indicating unit is clamped between the springs) and is inexpensive.

According to an aspect of the invention which may possibly be independently claimed, the latching mechanism may be configured to include a latch spring adapted to be biased via an actuator operable by the cover/access door and/or closing/locking mechanism into a latching function state so that upon reaching the sterile position by the effect of the shape-memory element the latch spring biased into its latching function automatically passes to a latching position in which the indicating unit is locked/supported in the sterile position even when the compressive force of the shape-memory element then decreases due to cooling of the interior of the container. The latch spring has a very simple design and thus is inexpensive as well as robust. In this way in a merely mechanical way, without any electric control or sensor system, the cover/access door and/or the closing/locking mechanism may be coupled to the sterilization indicator so as to constantly document the quality of the sterilizing operation (until unlocking/opening). Moreover, it is achieved in this way that this documentation is mechanically cleared automatically upon the first opening/unlocking of the container after the sterilizing operation in a simple manner (indicating unit automatically switches to the unsterile position).

Preferably the latch spring may be a separate component in the form of a leaf spring mounted to a housing of the sterilization indicator or to the container which is adapted to be brought in axial supporting engagement with the push element in the latching function state. In a top view the leaf spring may preferably take a U-shape having two legs extending in the axial direction of the push element between which legs the push element is axially guided, thus preventing the leaf spring from laterally sliding off the push rod. As an alternative, the latch spring may be a separate component in the form of a support plate/rod or a U-bracket which is movably supported, perpendicularly to the push element, via the actuator against a spring on a housing of the sterilization indicator or on the container and in the latching function state may be brought in axial supporting engagement with the push element (on the front end side). As a further alternative, the latch spring may form, as an integral element of the sterilization indicator, a resilient longitudinal portion of the push element which in the latching function state with an axial movement of the push element in the direction of the sterile position engages in a stop or latch pin on the sterilization indicator housing or on the container.

It is evident from the numerous alternatives mentioned that even further designs are imaginable for a latching mechanism in response to the structure of the container and/or the locking mechanism as long as the latching mechanism is so-to-speak armed by the container cover/access door and/or the closing/locking operation of the container and is triggered when the indicating unit switches to the sterile position so as to (mechanically) retain the indicating unit in the sterile position. It is of advantage that said latching position is lifted (quasi automatically) by the opening/unlocking operation of the container/container cover so that the indicating unit necessarily switches into the unsterile position thereof again. Preferably this is done by the force exerted by the cover and/or closing mechanism on the latching element to tension the latter into the latching function state being neutralized upon unlocking and/or opening of the container. A counter-pressure spring then may move the released latch element back into the disengaged position thereof.

Preferably the shape-memory element is a NiTi memory-metal helical compression spring which, when a temperature of approx. 90° C. is reached or exceeded, produces a spring-loaded force higher than the restoring force of the restoring spring due to the temperature-dependent memory effect.

Hence, according to the invention also a sterile container for sterilization of medical, preferably surgical instruments is provided comprising a preferably box-shaped instrument holding body that is adapted to be closed by a container cover/access door, for which at least one manually operable closing/locking mechanism may be or is arranged on the holding body and/or on the container cover, and that is equipped or adapted to be equipped with the sterilization indicator according to the invention as afore-described.

For this, the sterile container may preferably include a mounting pattern or similar connecting device which is arranged/formed on the holding body and/or on the container cover and to which the sterilization indicator, preferably the indicator housing accommodating the sterilization indicator, may be optionally mounted. In this way sterile containers may be delivered custom-made with or without the sterilization indicator according to the invention, wherein it is also easily possible to refit or replace the container with a new sterilization indicator. It is basically possible to mount the sterilization indicator without casing directly within the container by attaching said components of the sterilization indicator directly to the container.

BRIEF DESCRIPTION OF THE DRAWING FIGURES

Hereinafter the invention shall be illustrated by way of a preferred embodiment with reference to the accompanying figures.

DETAILED DESCRIPTION

Figure 4:
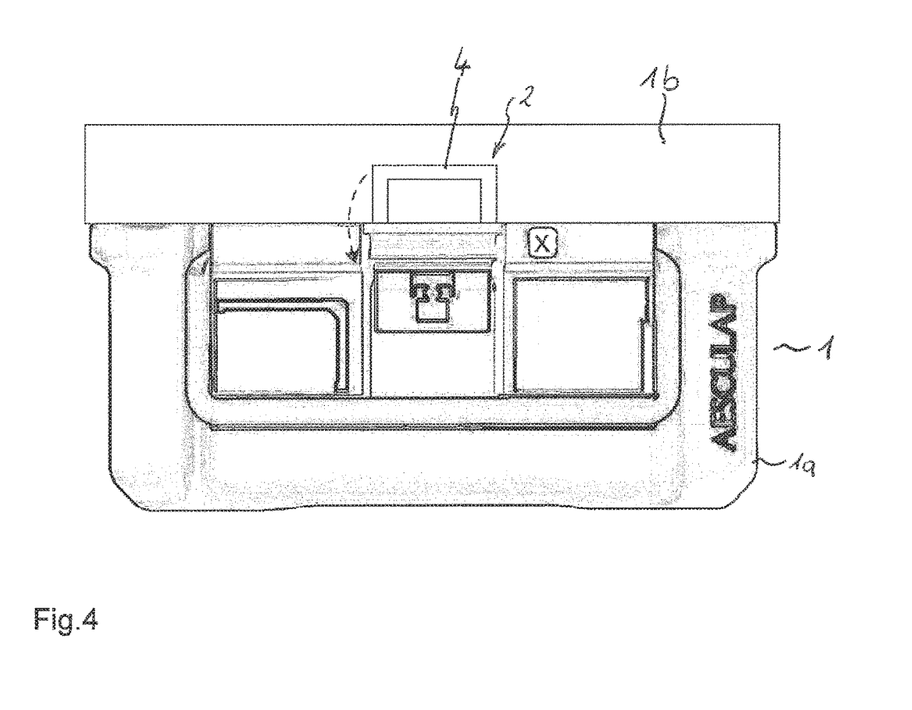
FIG. 4 shows the side view of a sterile container closed by a cover comprising the sterilization indicator according to the invention.
Figure 5:
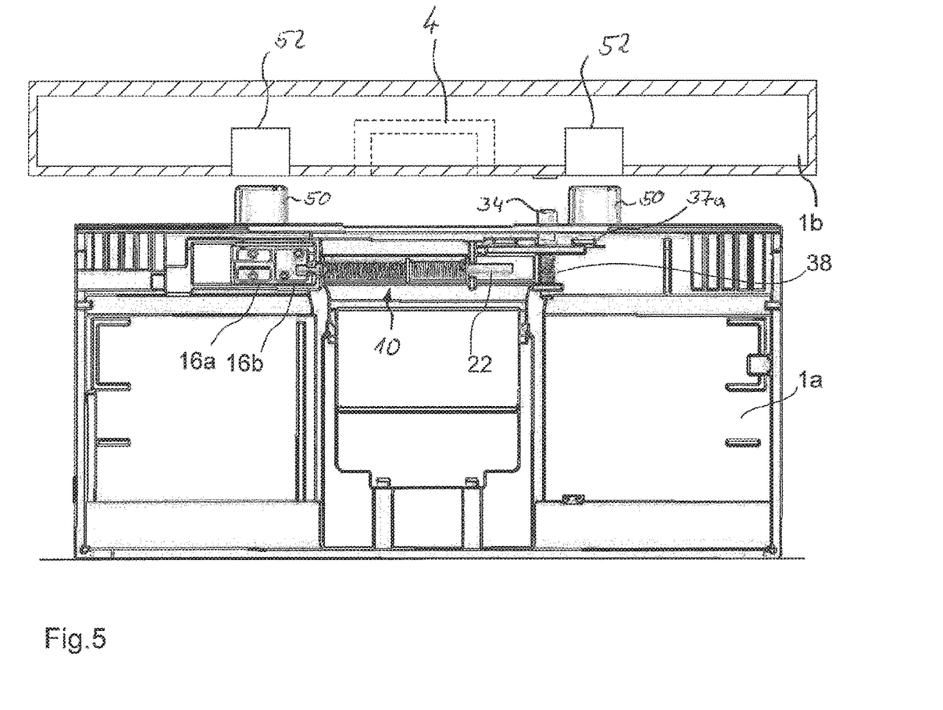
FIG. 5 shows the cut side view of an opened sterile container comprising the sterilization indicator according to the invention in an unarmed state.

In FIGS. 4 and 5 part of a sterile container known from prior art, e.g. according to the documents cited in the beginning, is schematically shown. The sterile container 1 includes a trough-shaped or box-shaped instrument holding body 1a being closable on at least one side (upper side) by means of a container cover 1b. At the cover 1b and/or at the holding body 1a a closing/locking mechanism 2 of a known design is arranged comprising a manually operable handle (e.g. buckle, lever etc.) 4 which is shown by way of example according to FIG. 4 by a bracket pivoted to the cover 1b, said bracket being adapted to be brought in clamping engagement with an undercut at the container trough 1a or at the cover 1b. It is expressly pointed out that also other designs for a closing/locking mechanism such as e.g. a sliding or turning lock, a door lock having pivoting snap-fits and similar known mechanisms may be provided. It is also basically imaginable not to lock the container cover 1b at all but to detachably press it onto the free edge of the container trough 1a similarly to a keep-fresh box cover. For this purpose, e.g. a groove into which the edge of the cover 1b can be impressed could be formed at the free edge of the container trough 1a.

A sterilization indicator 10 according to the invention is provided in the present case as a container-integral (fixedly installed) assembly as shown especially in FIG. 5. It is also imaginable, however, to provide the sterilization indicator 10 as an external/separate sub-assembly or assembly preferably including its own housing 12 (not shown in detail) which is optionally adapted to be mounted/installed at a predefined mounting position (mounting base) on the container 1.

The cover 1b is preferably hinged to the trough is or is freely detachable and on at least one support edge includes two recesses in the form of blind holes or slits 52 into which fixing pins or ribs 50 engage at the trough 1a so as to positively position the cover 1b in the closed position. Alternatively the trough 1a may also be formed to have grooves circumferential on the end face, as already indicated in the foregoing, in which the cover 1b can positively engage.

The sterilization indicator 10 includes an indicating unit 14 which from outside of the container 1 can indicate at least two container states in a preferably visually perceptible manner, viz. a sterile state (corresponding to a sterile position of the indicating unit) and an unsterile state (corresponding to an unsterile position of the indicating unit). For this purpose, the indicating unit 14 includes a slide 16 having two fields 16a, 16b separated in the sliding direction which are perceptible from outside through an inspection window 18 in the container 1 (see FIG. 2). To the fields 16a, 16b preferably symbols 20 for sterile and unsterile are applied.

A push element in the form of an actuating rod 22 which is supported to be axially movable along with the indicating unit 16 on the container 1 or on the housing 12 (not shown in detail) of the sterilization indicator 10 is coupled to the indicating unit 16. For this, on the container 1/indicator housing 12 at least two bearing bushes 24, 26 are formed in which the actuating rod 22 is slidably mounted at the two end portions thereof. The actuating rod 22 axially in the center includes a peripheral collar 28 dividing the actuating rod 22 into two axial portions. On one axial portion facing the indicating unit 16 a restoring helical compression spring 30 is wound around the actuating rod 22, said spring resting on the one fixed bearing bush 24 and on the peripheral collar 28 and thus (constantly) biasing the actuating rod 22 away from the bearing bush 24 on the indicating unit side. In this way the indicating unit 16 is (constantly) maintained in its unsterile position by a predefined (temperature-independent) restoring force of the restoring helical compression spring 30.

On the axial portion facing away from the indicating unit 16 a memory-metal helical compression spring (shape-memory element) 32 preferably made of NiTi memory metal is arranged which is equally wound around the actuating rod 22 and is supported against the peripheral collar 28 and the bearing bush 26 distant from the indicating unit and thus counteracts the restoring helical compression spring 30 (in a temperature-dependent way).

For the memory-metal helical compression spring 32 a material was selected which adopts its original shape when a temperature of approx. 90° C. is exceeded. That is to say, the memory-metal helical compression spring 32 is designed to exert a compressive force higher than the (constant/temperature-independent) restoring force of the restoring helical compression spring 30 on the actuating rod 22, when the predetermined sterilizing temperature of preferably 90° C. is exceeded. Hence the actuating rod 22 is displaced against the restoring helical compression spring 30, when the predetermined sterilizing temperature is exceeded, and consequently the indicating unit 16 is switched to its sterile position.

Figure 1:
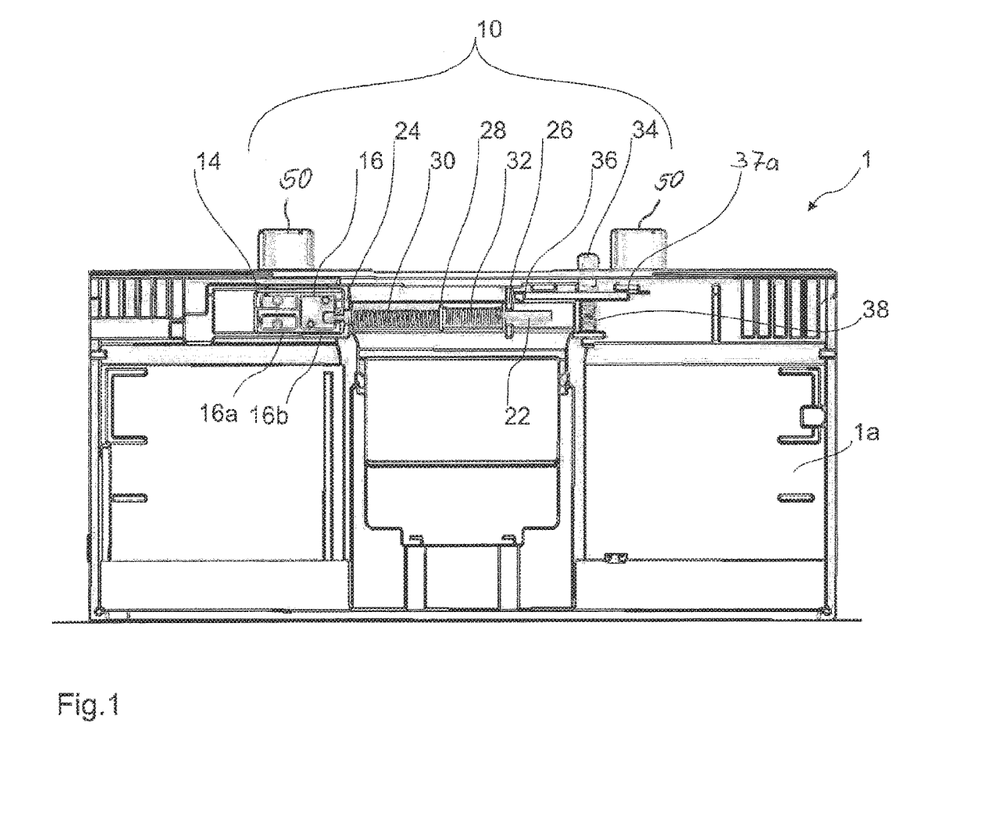
FIG. 1 shows a sterilization indicator (optionally) mounted in a sterile container/sterile container cover according to a preferred embodiment of the invention in an unarmed state.

As one can further infer from FIG. 1 and FIG. 5, the sterilization indicator 10 according to the invention in addition includes a latching mechanism. In the present case, the latter includes an actuating pin 34 supported to be axially (in the closing direction of the cover 1b) movable on the container 1 or on the indicator housing 12, wherein the axial direction thereof thus extends substantially perpendicularly or at an angle with the axial direction of the actuating rod 22. The actuating pin 34 is either operatively connected to the closing mechanism 2 such that the actuating pin 34 is axially displaced upon actuation of the closing mechanism 2, or, as concretely illustrated in the present example, the actuating pin 34 axially protrudes from the container 1 in the direction of the cover 1b and is axially pressed into the container 1 when the cover 1b is slid/attached into the closing position. It is pointed out in this context, however, that there are also other options of coupling between the cover and the latching mechanism (e.g. in the area of the hinged support) or between the closing/locking mechanism and the latching mechanism (by interposed actuating levers, for example).

Figure 7:
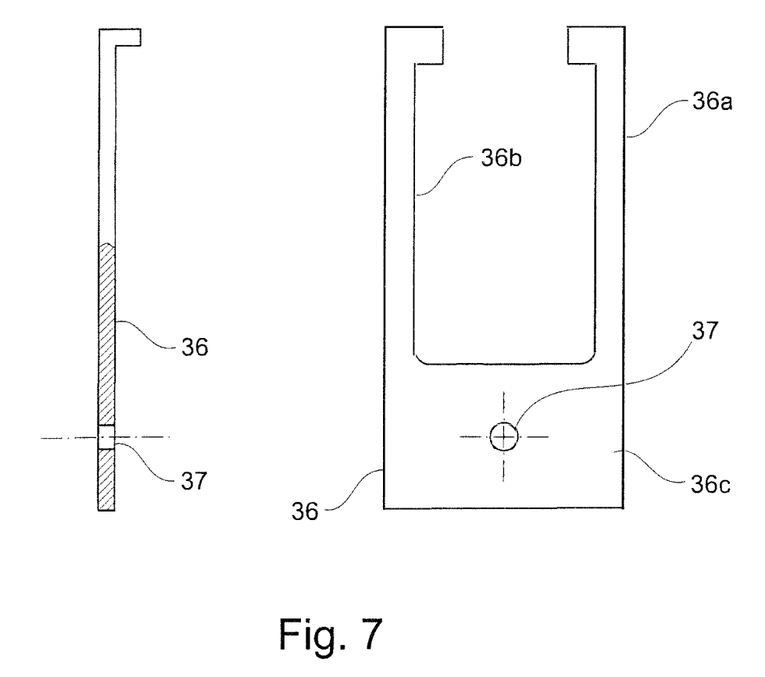
FIG. 7 shows the top view and side view of a latch spring according to the present invention.

A latch spring 36 in the form of a spring tongue is fixed to the actuating pin 34. Said spring tongue may be a simple leaf spring or in a top view may have a profile as indicated in FIG. 7. In the latter case, in a top view the spring tongue 36 is U-shaped having two legs 36a, 36b spaced in parallel and a cross-beam 36c in which a through hole 37 is formed. The free ends of the legs 36a, 36b are bent by approx. 90° relative to supporting faces. The through hole 37 has a diameter that enables the actuating pin 34 to be inserted there through.

Finally a biasing spring 38, preferably helical spring, is provided around the actuating pin 34, said spring resting, on the one hand, on the container 1 or the indicator housing 12 and, on the other hand, on the spring tongue 36 and thus biasing the actuating pin 34 in the axial direction against the actuating force by the closing/locking mechanism or against the container cover (out of the container 1) and, accordingly, initially forcing the spring tongue 36 against a container-side/housing-side stop 37a. In this (installed) position the spring tongue 36 is provided at a parallel distance from the actuating rod, as especially represented in FIG. 5.

The spring tongue 36 furthermore is arranged, with a predefined axial displacement of the actuating pin 34 against the biasing spring 38 (corresponding to the pin portion protruding from the container 1) and triggered by the closing/locking mechanism or the attachment of the cover, to be substantially aligned on an axis line relative to the actuating rod 22, i.e. to be placed behind the one end face of the actuating rod 22 and thus to serve as an axially acting displacement stop for the actuating rod 22. If, on the other hand, the actuating force acting on the actuating pin 34 is removed (e.g. by opening the cover 1b and/or by actuating the locking mechanism 2), the biasing spring 38 forces the actuating pin 34 back into its design position against the stop 37a where the spring tongue (latch spring) 36 again is positioned substantially in parallel to (at a parallel distance from) the actuating rod 22.

Figure 2:
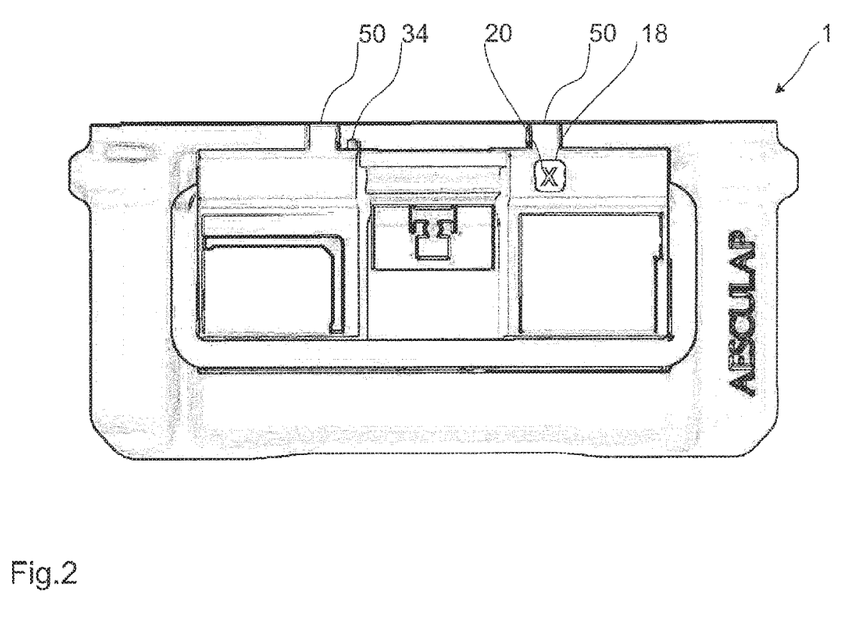
FIG. 2 shows the side view of a sterile container closing mechanism comprising the sterilization indicator according to the invention.

The functioning of the indicator according to the invention shall be described hereinafter by way of FIGS. 1 and 2.

Figure 6:
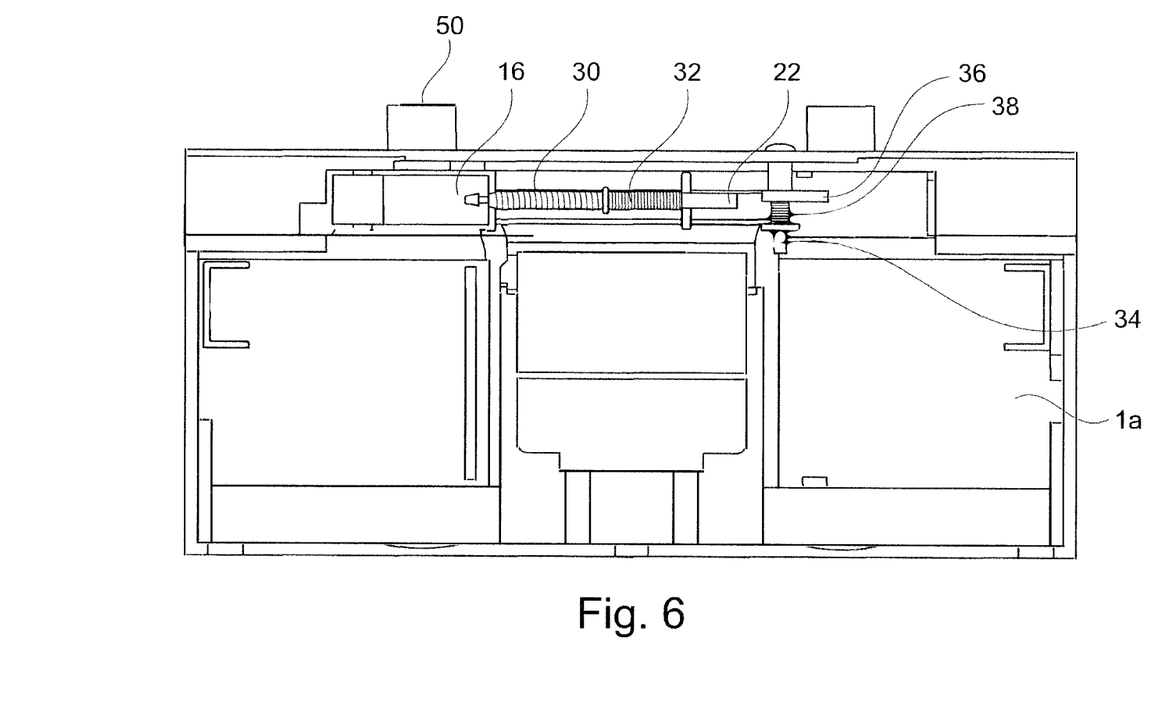
FIG. 6 shows the cut side view of an opened sterile container comprising the sterilization indicator according to the invention in an armed state.

By locking the container closing/locking mechanism (e.g. pivoting the bracket 4) and/or, as shown, by closing the cover 1b first the actuating pin 34 is axially displaced (into the container) against the biasing spring 38. The spring tongue/latch spring 36 laterally contacts the actuating rod 22 and thus is initially resiliently bent/biased. This state is shown in FIG. 6. In this state according to FIG. 6, for the time being the latching mechanism is armed only into its latching function (but not yet its latching position). In the case of a U-shaped spring tongue, as shown in FIG. 7, the actuating rod is partly provided between the resiliently bent spring tongue legs 36a, 36b and is thus axially guided between said legs 36a, 36b.

When the closed and/or locked container 1 is now heated to a defined sterilization temperature (more than/equal to 90° C.), the memory-metal helical compression spring 32 produces a predefined compressive force onto the actuating rod 22 which is higher than the (constant/temperature-independent) restoring force of the restoring helical compression spring 30, thus causing the actuating rod 22 to be axially displaced in the direction of the indicating unit 16. Hence the indicating unit 16 is also displaced and thus switched from the unsterile position into a sterile position, which according to FIG. 2 is perceptible from outside through the inspection window 20 in the container 1. At the same time, the spring tongue 36 and, resp., the legs 36a, 36b resiliently snap axially behind the end face of the actuating rod 22 due to the axial displacement of the actuating rod 22. In the case of the U-shaped spring tongue 36 according to FIG. 7, the legs 36a, 36b prevent the actuating rod 22 from laterally slipping off during axial movement thereof.

When the container 1 now cools down to a temperature below the sterilization temperature (e.g. 80° C.), the spring force of the memory-metal helical compression spring 32 is reduced to a value below the restoring spring force. However, the restoring helical compression spring 30 initially is not adapted to displace the actuating rod 22 (to the right according to FIG. 1) into its design position as it is supported by the spring tongue 36 of the latching device actuated by the cover and/or the latching mechanism as axial stop. In this way the indicating unit 16 is retained in the sterile position and thus documents (in a mechanical way) that the sterilizing operation has been carried out correctly.

When the closing/latching mechanism 4 of the sterile container 1 is actuated for opening and/or the cover 1b is opened, the actuating pin 34 of the latching mechanism operatively connected thereto is released, thus causing the latter to be axially displaced by means of the biasing spring 38 into a disengaged position of the spring tongue 36 relative to the actuating rod 22 in the direction of the stop 37a (design position). Since the actuating rod 22 is no longer supported by the spring tongue 36, the latter is axially displaced by the restoring spring 30, thus causing the indicating unit 16 to be switched to its unsterile position (see FIG. 2). The documentation of the sterile state of the container 1 is thus automatically (necessarily) cancelled by first unlocking of the closing/locking mechanism and/or opening of the cover 1b after the last sterilizing operation and is retained in the unsterile position even when the container 1 is closed and/or locked again.

In this context, it is once again referred to the fact that the latching mechanism need not be operatively coupled directly to the closing/locking mechanism 4, but may also be (indirectly) actuated by the container cover 1b itself, wherein also a (necessary) combination of the cover closing operation and the locking operation would be imaginable for actuating the latching mechanism. I.e. upon opening and closing the container cover 1b (possibly in combination with the locking/unlocking of the locking mechanism 2) the actuating pin 34 of the latching mechanism is axially displaced and in this way the latching mechanism is armed, as shown in FIG. 6, or is released (unarmed), as shown in FIG. 5. In addition, the spring tongue 36 could be replaced by a rigid support element which is then pivoted on the actuating pin 34 and is stabilized, for example, by the biasing spring 38 resting thereon. Finally it is also possible to fix the spring tongue 36 directly to the container 1 or to the indicator housing 12 and to provide the actuating pin 34 as a pressing element for biasing the spring tongue 36 resiliently in the direction of a supporting position with the actuating rod 22.

Figure 3:
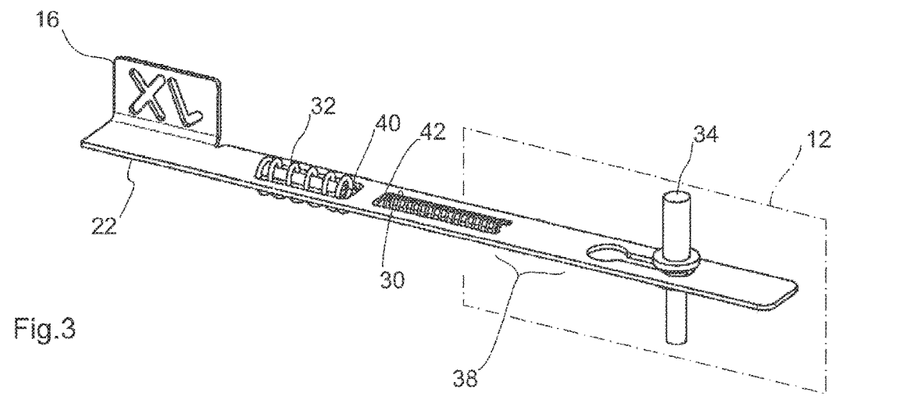
FIG. 3 shows an alternative design of the sterilization indicator according to the invention.

Finally FIG. 3 illustrates a further alternative configuration of the afore-described design.

In this case the push element 22 is not in the form of an actuating rod but in the form of a flat push strip (stamped part, where appropriate) having two axially spaced slit-shaped receiving windows 40, 42 into which the two springs (memory-metal helical compression spring 32 and restoring helical compression spring 30) are inserted so that on a respective end side they rest on the push strip 22 and on a respective other end side they rest on the container 1/indicator housing 12 (shown only schematically in FIG. 3), as this has been described also by way of FIG. 1. Furthermore, in FIG. 3 the push strip 22 is preferably not coupled to the indicating unit 16 but supports the same or is integrally formed with the same, respectively.

Ultimately, the biasing spring 38 of the latching mechanism is not a separate component, as shown in FIG. 1, but the push strip 22 includes a resilient longitudinal portion 38 constituting sort of a spring tongue for forming the biasing spring.

When the actuating pin 34 is consequently axially displaced from its design position by the container cover and/or the closing/locking mechanism, the push strip 22 is thus biased in the bending direction at its resilient portion 38. When the push strip 22 now is displaced by the spring force of the memory-metal helical compression spring 32 upon reaching/exceeding the sterilization temperature, the resilient portion 38 of the push strip 22 snaps behind a stop (not shown) at the container 1 or the indicator housing 12 and in this way axially supports the push strip 22 against the restoring spring 30. Hence the latter is retained in the sterile position even when the temperature falls below the sterilization temperature (drop of the spring force of the memory-metal helical compression spring 32).

When finally the actuating pin 34 is axially released by unlocking and/or opening the container 1, the resilient portion 38 of the push strip 22 triggers so that the restoring spring 32 can axially move the push strip 22 from the sterile position back into the unsterile position. Hence also in this case the indication of the sterile position of the container 1 and of the content thereof, respectively, is cancelled.

Concluding, the invention discloses a sterilization indicator 10 for a sterile container 1 having a shape-memory element 32 in the form of an axially acting compression spring, preferably of the helical spring type, which, when a predetermined sterilization temperature is reached or exceeded, subjects an indicating unit 16 to a defined axial compressive force, said indicating unit in turn being biased by means of a restoring spring 12, preferably of the helical spring type, acting independently of temperature in the counter-direction of the shape-memory element 32 by way of a restoring force which is smaller than the defined axial compressive force, and having a latching mechanism which can be actuated by a manually operable closing or locking mechanism of the sterile container and/or by the container cover and/or an element (e.g. lever, button etc.) attached thereto and is designed such that after or upon closing and/or locking of the sterile container 1 it retains the indicating unit 16 in a sterile position, once said unit has been moved into the sterile position by the shape-memory element 32, and upon opening and/or unlocking of the sterile container 1 below the sterilization temperature it releases the indicating unit 16, whereupon the restoring spring 30 moves the indicating unit 16 back into an unsterile position.

The invention claimed is:

1. A sterile container for sterilization of medical instruments comprising an instrument holding body closable by a container cover for which at least one manually operable closing/locking mechanism is arranged on the holding body and/or on the container cover, the sterile container comprising a sterilization indicator, wherein the sterilization indicator comprises a shape-memory element in the form of an axially acting compression spring, made of memory material which, when a predetermined sterilization temperature is reached or exceeded, subjects an indicating unit to a defined axial compression force, said indicating unit in turn being biased by a restoring spring functioning independently of temperature, in a counter-direction of the shape-memory element by way of a restoring force which is smaller than the defined axial compressive force, and comprising a latching mechanism which is actuated by at least one of: (1) a manually operable closing or locking mechanism, (2) a container cover of the sterile container, and (3) an element attached thereto and designed such that by closing and/or locking of the sterile container it retains the indicating unit in a sterile position, once said unit has been moved into the sterile position by the shape-memory element, and by opening and/or unlocking of the sterile container below the sterilization temperature it releases the indicating unit, whereupon the restoring spring moves the indicating unit back into an unsterile position.

2. The sterile container according to claim 1, comprising a mounting pattern which is arranged at the holding body and/or at the container cover and on which the sterilization indicator can be mounted.

3. The sterile container according to claim 2, further comprising an indicator housing accommodating the sterilization indicator, the indicator housing adapted to be mounted on the mounting pattern.

4. The sterile container according to claim 3, wherein the sterilization indicator comprises a push element in the form of an axially movable push rod or push strip, with which at least the shape-memory element is in axial compression engagement and which actuates the indicating unit perceptible from outside of the container into the sterile position and/or unsterile position, or which supports or forms the indicating unit.

5. The sterile container according to claim 4, wherein the latching mechanism includes a supporting element adapted to be biased via an actuator operable by the closing/locking mechanism or by the container cover into a latching function state so that upon reaching the sterile position the support element biased into its latching function automatically adopts a latching position in which the indicating unit is locked in the sterile position even when afterwards the compressive force of the shaped-memory element decreases as the interior of the container cools down.

6. The sterile container according to claim 5, wherein the supporting element is a latch spring.

7. The sterile container according to claim 6, wherein the latch spring is an integral element of the sterilization indicator and forms a resilient longitudinal portion of the push element which in the latching function state upon axial displacement of the push element in a direction of the sterile position enters into support engagement with a stop or locking pin at the indicator housing or at the container.

8. The sterile container according to claim 5, wherein the supporting element is a leaf spring, mounted on the indicator housing or on the container, said leaf spring in the latching function state in which it is resiliently adjacent to the side of the push element being adapted to be brought in supporting engagement with the push element at the end face, once the push element has been axially displaced by the shape-memory element.

9. The sterile container according to claim 8, wherein the leaf spring has a U-shape and is mounted on the indicator housing or on the container.

10. The sterile container according to claim 5, wherein the supporting element is a support plate/rod which is movably supported perpendicularly to the push element via the actuator against a spring on the indicator housing or on the container and in the latching function state is adapted to be brought in axial support engagement with the push element, once the push element has been axially displaced by the shape-memory element.

11. The sterile container according to claim 4, wherein the restoring spring is in axial compression engagement with the push element.

12. The sterile container according to claim 3, wherein the shape-memory element and the restoring spring rest on the indicator housing or on the sterile container forming a counter-bearing.

13. The sterile container according to claim 1, wherein the shape-memory element is a NiTi memory-metal compression spring which, when a temperature of approximately 90° C. is exceeded, produces a spring-loaded force higher than a restoring force of the restoring spring due to a temperature-dependent memory effect.

14. The sterile container according to claim 13, wherein the compression spring and the restoring spring functioning independently of temperature are configured in a helical spring design.

\* \* \* \* \*